(12) United States Patent
Davies et al.

(10) Patent No.: US 7,865,975 B2
(45) Date of Patent: Jan. 11, 2011

(54) WAIST BELT HAVING ARTICULATED SHOULDER STRAPS

(76) Inventors: Richard Davies, 3128 Fawnwood CV, Sandy, UT (US) 84092; Christopher A. Davies, 1178 Redding Ct., Sandy, UT (US) 84094

( * ) Notice: Subject to any disclaimer, the term of this patent is extended or adjusted under 35 U.S.C. 154(b) by 198 days.

(21) Appl. No.: 11/540,275

(22) Filed: Sep. 29, 2006

(65) Prior Publication Data

US 2007/0074327 A1     Apr. 5, 2007

Related U.S. Application Data

(60) Provisional application No. 60/722,815, filed on Sep. 30, 2005.

(51) Int. Cl.
*A41F 19/00*     (2006.01)
(52) U.S. Cl. .......................................................... 2/310
(58) Field of Classification Search ............... 2/311, 2/312, 44, 45, 338, 310, 467, 69
See application file for complete search history.

(56) References Cited

U.S. PATENT DOCUMENTS

| 5,040,524 | A | * | 8/1991 | Votel et al. ..................... 602/19 |
|---|---|---|---|---|
| 5,319,806 | A | * | 6/1994 | Hermann et al. ................ 2/461 |
| 5,497,923 | A | * | 3/1996 | Pearson et al. ............... 224/639 |
| 5,499,965 | A | * | 3/1996 | Sanchez ....................... 602/19 |
| 5,834,789 | A | * | 11/1998 | Marchione ................ 250/516.1 |
| 5,909,802 | A | * | 6/1999 | Puco et al. ...................... 2/102 |
| 6,766,532 | B1 | * | 7/2004 | Cabana ............................. 2/44 |
| 7,036,628 | B2 | * | 5/2006 | Wilcox et al. ................... 182/9 |

* cited by examiner

*Primary Examiner*—Tejash Patel

(57) ABSTRACT

A wearable device to comfortably and ergonomically transfer substantially all of the weight of a heavy protective garment from a wearer's shoulders, neck and back to the wearer's waist, in a manner that does not interfere with the normal and necessary movement and range of motion of the wearer. The device transfers the weight of the protective garment from the shoulder area of the wearer to a belt at the waist/hip area of the wearer via a vertical support member(s) that incorporate(s) articulating and adjustable elements which permit the device to accommodate the natural movement of the wearer's body at the waist, back, neck and shoulders while transferring the weight of the protective garment to the waist/hip area of the wearer. The subject device may also be incorporated into or made part of a protective garment.

3 Claims, 4 Drawing Sheets

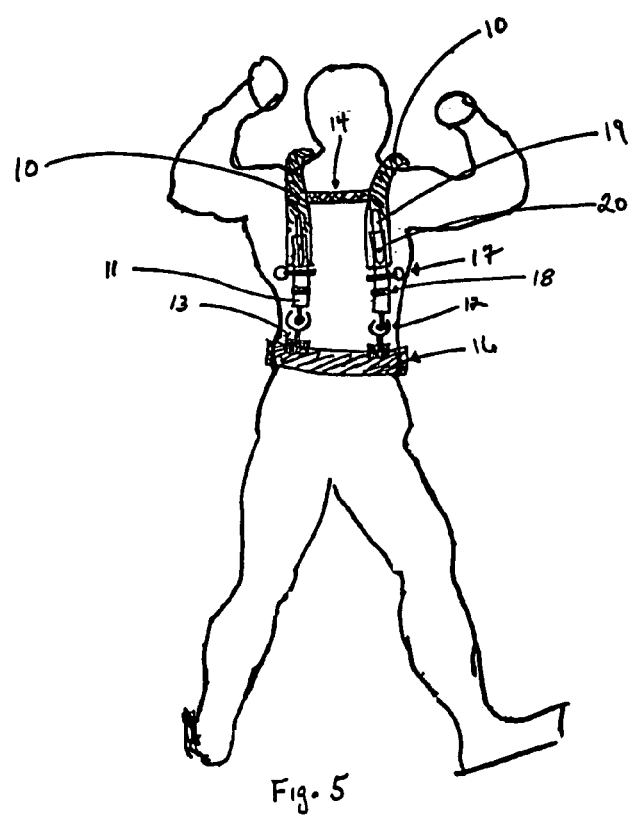
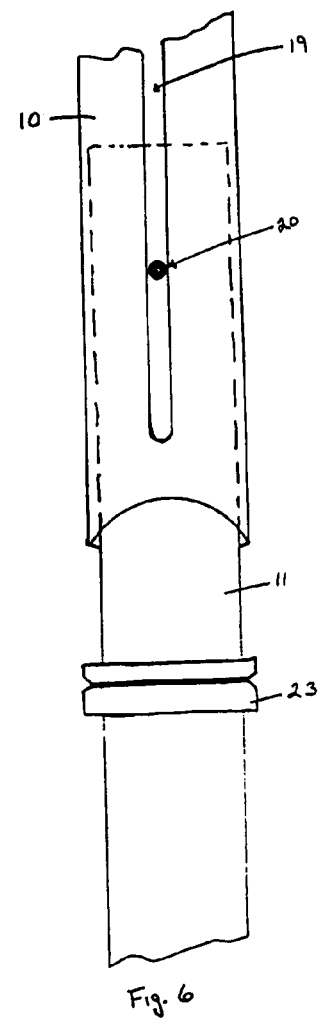
Fig. 5
Fig. 6

WAIST BELT HAVING ARTICULATED SHOULDER STRAPS

RELATED APPLICATION

This application claims priority from U.S. Provisional Patent Application No. 60/722,815, filed on Sep. 30, 2005 and titled, Device to Ergonomically Transfer Weight of a Heavy Apron or Garment from the Shoulders of the Wearer to the Wearer's Hips

BACKGROUND OF THE INVENTION

It is well known that persons required to wear heavy protective upper body garments often suffer from neck, back and shoulder pain, as a direct result of the weight of such heavy protective garments. This problem is exacerbated as the weight and wearing time of the garment increase.

One common use of such heavy protective garments is to provide the wearer with protection from ionizing radiation, such as X-rays. For example, this need applies to medical, scientific and industrial personnel as they use X-ray imaging in medical procedures and in the inspection and analysis of materials.

Lead is the common shielding material used in these X-ray protective garments, causing the garments to be very heavy, often weighing in excess of 15 pounds. Further, many of these X-ray procedures are of a long duration. For example, medical procedures requiring X-ray imaging may extend for many hours and technicians and doctors may also have a number of shorter procedures scheduled one after the other, resulting in extended wearing time of these heavy protective garments.

Another common area for the use of heavy protective garments is in fire fighting. Firefighters often wear heavy heat/fire protective coats for long periods of time, as well as wearing heavy equipment (such as breathing apparatus) that all bear down on the shoulders The heavy weight of these protective garments and other shoulder born equipment and the long periods that they must sometimes be worn combine to create fatigue, pain and even can lead to chronic pathology in the back/spine, neck and shoulders of some wearers.

Others have attempted to address this well recognized problem by proposing devices that intend to transfer the weight of the protective garment from the shoulders to the waist and hips of the wearer. For example, Maine (U.S. Pat. No. 3,996,620) and also McCoy (U.S. Pat. No. 4,441,025) describe radiation protection aprons with securing flaps, wing panels and ties that are intended to more evenly distribute the weight of the garment between the wearer's shoulders and waist. Others, such as Hoffman (U.S. Pat. Nos. 4,527,288 & 4,602,386) describe means for supporting part of the weight of the garment on the wearer's belt or trousers with the use of clips, hooks or brackets that are integrally attached to the protective garment. Still others, including Herbert (U.S. Pat. No. 4,417,146 and also Marchion U.S. Pat. No. 5,834,789) describe radiation protective garments that include in their design various, one piece vertical stiffeners or stay members that are incorporated into the garment and secured by a strap or belt at the wearer's waist, such that the weight of the apron is transferred, via the vertical stiffeners or stay members to the wearer's waist.

Marchion (U.S. Pat. No. 5,844,246) also teaches a radiation protective garment that incorporates rigid or semi-rigid stay member(s) into the garment. These one piece stay member(s) are intended to transfer the weight of the garment to the waist/pelvic area of the wearer by means of securely cinching a support belt over the bottom portions of the stay member(s) at the waist of the wearer. '246 further claims a method for supporting a radiation protection garment with a stay member(s) that is worn under the garment and that is independent of the garment.

Effectively, '246 and the X-ray Attenuating Apron taught by Linton ('146), for example, place the wearer's upper body (above the waist) in a confining cage, comprised of the rigid/semi-rigid stay member(s), support belt secured tightly around the wearer's waist, and further confined by the garment being supported by said stay member(s). This situation limits the wearer's necessary normal range of motion and the ability to easily and naturally carryout desired and necessary work functions.

It is therefore clear that the teachings of '246 and others, for a method of supporting the weight of a protective garment, describes a method that trades off the loss of the wearer's normal range of motion in order to achieve effective support/weight transfer of the garment, as is the stated objective of this prior art.

Further, '246, teaching to raise a stay member(s) after tightly cinching the belt over the bottom portion of the stay member(s) (and after the wearer has put on the garment over the stay members) would require significant manual force and would require this same difficult readjustment each time the device is removed and put back on by the same wearer.

'246 describes a one piece stay member, attached at its lower end to a support belt and extending from the waist area portion of the wearer over a respective shoulder of said wearer. '246 further describes different length stay member(s) to accommodate different size wearers and different size garments. '246 does not teach or suggest any varying of the length of a given stay member(s) to reduce the number of different sizes of said stay member(s) necessary to fit persons of differing heights.

Hoffman ('288 & '386) does not teach the use of vertical support stays, but rather hooks incorporated into the garment to support the garment on the waist belt of the wearer. This method can transfer only the weight of the lower part of the garment (portion below said hook) to the waist belt and does not address the weight of the portion of the garment above the hooks/waist area of the wearer.

In summary, the prior approaches to address the need to transfer the weight of a heavy protective garment off the shoulders, back and neck of the wearer to the wearer's waist and hips involve either protective garments that incorporate rigid stay members, attached to a waist belt, as a part of the garment, or a support belt (worn about the waist) to which is/are rigidly attached one or more to rigid or semi-rigid stay members; or a clipping systems that transfer only a portion of the weight of the garment off of the wearer's shoulders, to the wearer's waist/hip area. All of these approaches, as discussed above, have certain disadvantages that limit their utility and comfort by limiting or interfering with the freedom of movement of the wearer.

SUMMARY OF THE INVENTION

The subject invention of this application addresses the need to ergonomically transfer all or substantially all of the weight of a heavy garment that would otherwise, without the use of this invention, be born solely on the wearer's shoulders, to the wearer's waist It is an intention of this invention to bear and transfer such garment weight in a manner that does not interfere with the wearer's ease of movement and the full range of motion of the wearer's arms, shoulders and back, by disclosing articulating, adjustable, multiple piece vertical support member(s) disposed over and behind each shoulder of the wearer and interconnected one with another and further supported upon a belt around the wearer's waist/hip area. It is also an objective of this invention that a single device, based on the teachings of this invention, accommodates wearers of varying heights. Further still, it is an objective of this invention to provide a device that a wearer can remove and subsequently put back on their body, without the need for readjustment of the said device. It is also an objective of this invention to allow the wearer to select the tightness of the waist belt portion of the subject device based primarily on wearer comfort, without relaying on the tightness of the waist belt as the means by which to adjust and secure the vertical support assembly of the device, which serves to support the protective garment and transfer the weight of the garment to the wearer's waist/hip area.

A further objective of this invention is a protective garment support device that can have limited downward movement, in order to support the weight of a protective garment (transferring said weight from the wearer's shoulders to the wearer's waist/hips) without limiting the otherwise available upward movement of said garment support device, when such upward movement is required to accommodate the upward movement of the wearer's shoulders, e.g., 'as in 'shrugging' ones shoulders or reaching overhead.

A still further objective of the invention is a protective garment support device, with the above described elements, that is incorporated into the construction of a protective garment.

DESCRIPTIONS OF THE DRAWINGS

FIG. 5 is a perspective back view of the invention showing its parts and its relative position on a wearer, per the preferred embodiment.

FIG. 6 is a cross sectional side view of the support rod/shoulder support tube as slidably attached one to the other with a locking collar to limit compression of the two parts without the said locking collar restricting extension of the parts, per the preferred embodiment.

DESCRIPTION OF THE PREFERRED EMBODIMENT

Figure 1:
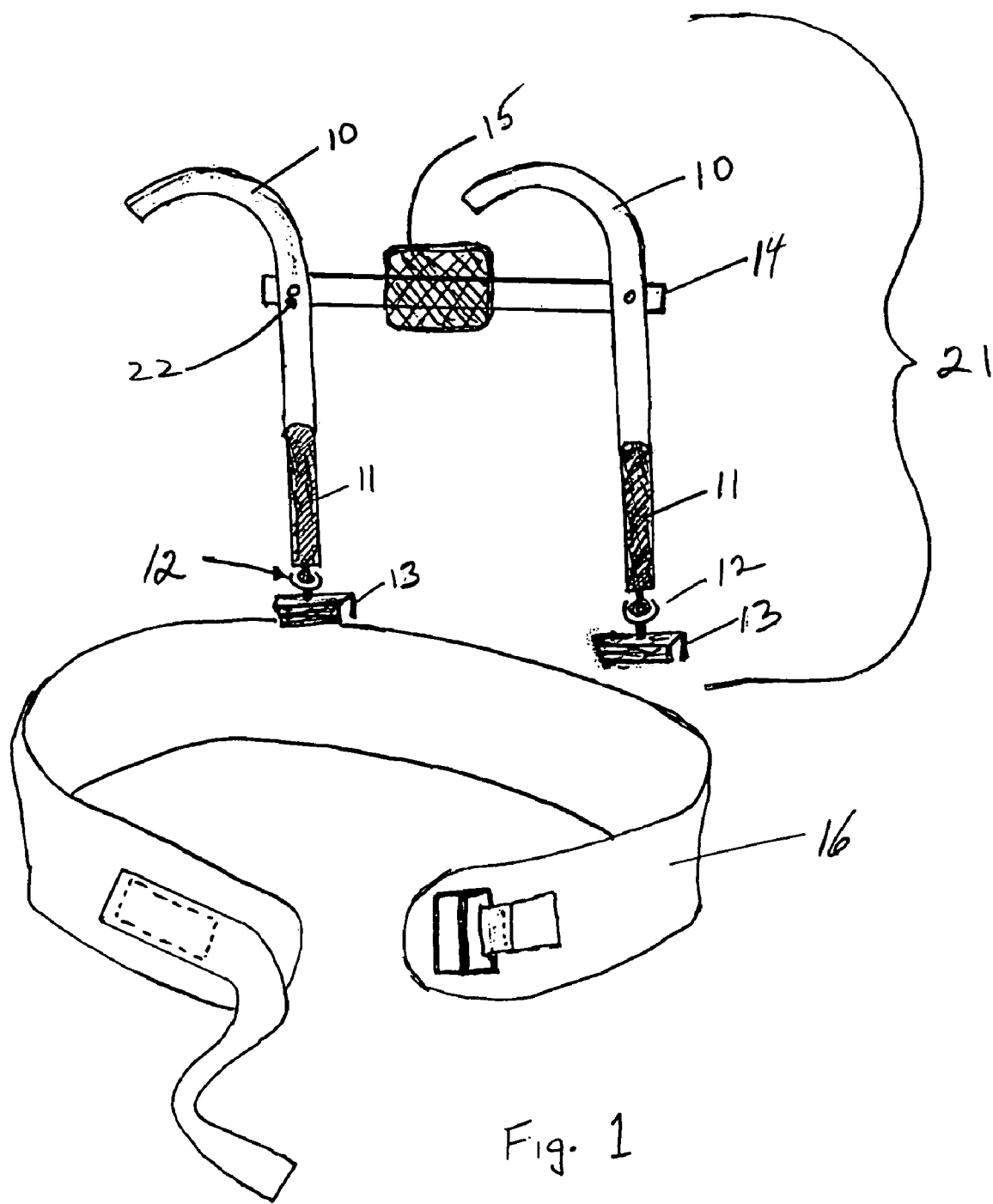
FIG. 1 is a perspective front view of the invention showing the garment support assembly and its parts and also showing the waist belt, per the preferred embodiment.
Figure 2:
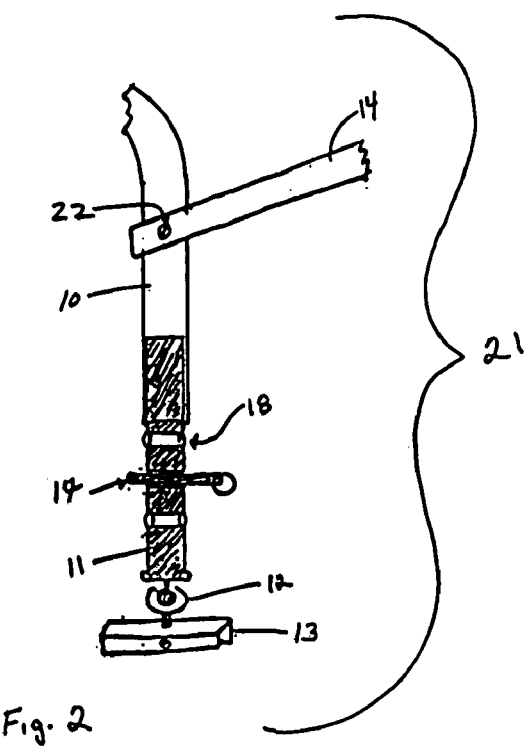
FIG. 2 is a cross sectional side view of a single support assembly, per the preferred embodiment.

In a preferred embodiment of this invention there is a garment support assembly 21 and a waist belt 16. The weight of the garment at the wearer's shoulders is born on two curved 'cane' shaped shoulder support tubes 10, each extending from in-front of a wearer's shoulders, over the wearer's shoulders and then continuing a portion of the distance from the wearer's shoulders down toward his/her waist, but not extending to the waist area of said wearer.

These shoulder support tubes, which may be fabricated of metal or plastic tubing, attach generally along their vertical axis to the first and second ends of a horizontal back support bar 14, such that the three members (two shoulder support tubes and one back support bar) generally form the capital letter 'H' with the two shoulder support tube's representing the vertical portions of the 'H' and the back support bar serving as the horizontal portion of the capital letter 'H'. The attachment of the back support bar to each shoulder support tube is by a means that allows the back support bar to pivot in a plane that is generally in line with the vertical axis of the shoulder support tube (such means of attachment may be a pin through a hole common to both parts) 22. Further, a pad 15 (such as of a common foam rubber material) is attached to the back support bar, generally midway between the two shoulder support tubes and between the back support bar and the back of the wearer. The back support bar, with its attachment to the two shoulder support tubes and the said pad, serve to stabilize one shoulder support tube relative to the other shoulder support tube and to the wearer, while allowing for a range of independent vertical movement of each shoulder support tube and retaining the general parallel orientation of the shoulder support tubes, one to another. The back support bar may be fabricated of metal or plastic sheet material.

Figure 3:
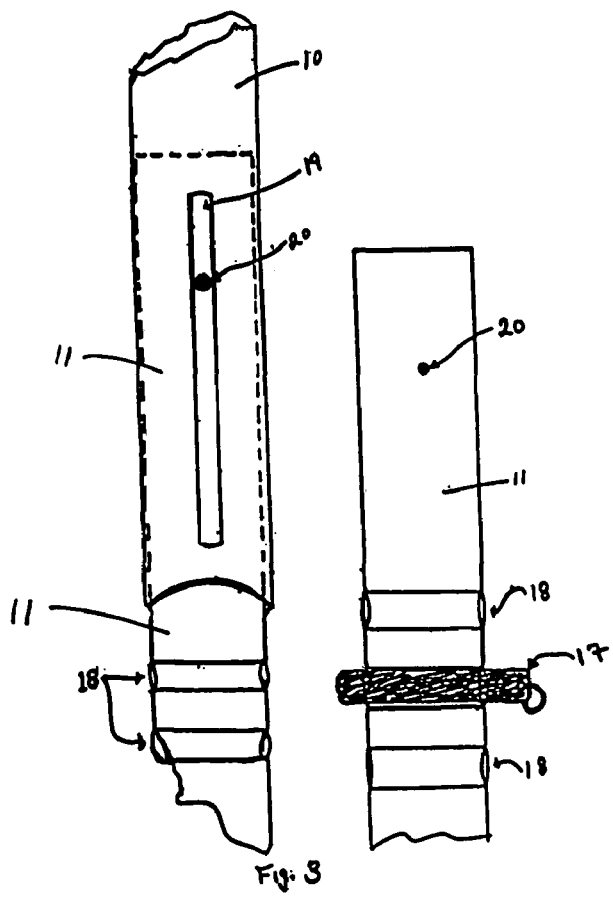
FIG. 3 is a cross sectional side view of the support rod and the support rod/shoulder support tube as slidably attached one to the other, per the preferred embodiment.

Inserted into the non-curved, lower portion of each shoulder support tube 10 is a support rod 11. The shoulder support tube and support rod are slideably attached to one another, such that the two members are free to move relative to one another along their common vertical/long axis in a telescoping fashion. In this manner the combined length of the shoulder support tube/support rod assembly may be lengthened or shortened, within a defined range of travel FIG. 3. This range of travel may be limited by incorporating a slot 19 along the vertical axis of the shoulder support tube, in the side wall of the shoulder support tube 10 and inserting a post 20 into a hole in the side of the support rod 11, such that the said post travels within the said slot, in the shoulder support tube 10. Travel of the shoulder support tube/support rod assembly is limited by the length of slot 19. Further, the telescoping distance of travel of the shoulder support tube relative to the support rod may be varied by inserting a pin 17 into holes 18 placed in the horizontal axis of the support rod 11 or by positioning a slideable/locking collar 23 on the support rod 11 that limits the ability of the shoulder support tube/support rod assembly to shorten, without limiting the otherwise full extension travel of the shoulder support tube/support rod assembly, as allowed by the post 20 traveling in slot 19; FIGS. 3 & 6. The support rod 11 may be fabricated of a metal or plastic rod material with an outside diameter that will fit into the inside diameter of the shoulder support tube 10.

Further, the lower ends of the support rod 11 attach to the upper portion of an articulating union 12, such as a ball and socket assembly. The lower portion of the articulating union is then joined to a belt attachment portion 13 that is suitable for attachment to a waist belt 16. Such waist belts are commonly available, such as the athletic back support belt by Altus Athletic Mfg. Co. Inc. Such support belts incorporate a buckle and strap for tightening the belt around the waist of the wearer. The belt attachment portion 13 may be fabricated of metal or plastic material and incorporates a simple screw clamping design or other attachment design, well know to the industry.

Taken together, the shoulder support tube 10, support rod 11, back support bar 14, adjustment pins 17/collars 23, upper & lower portions of the articulating union 12 and the belt attachment portion 13 are herein referred to as the garment support assembly 21.

Figure 4:
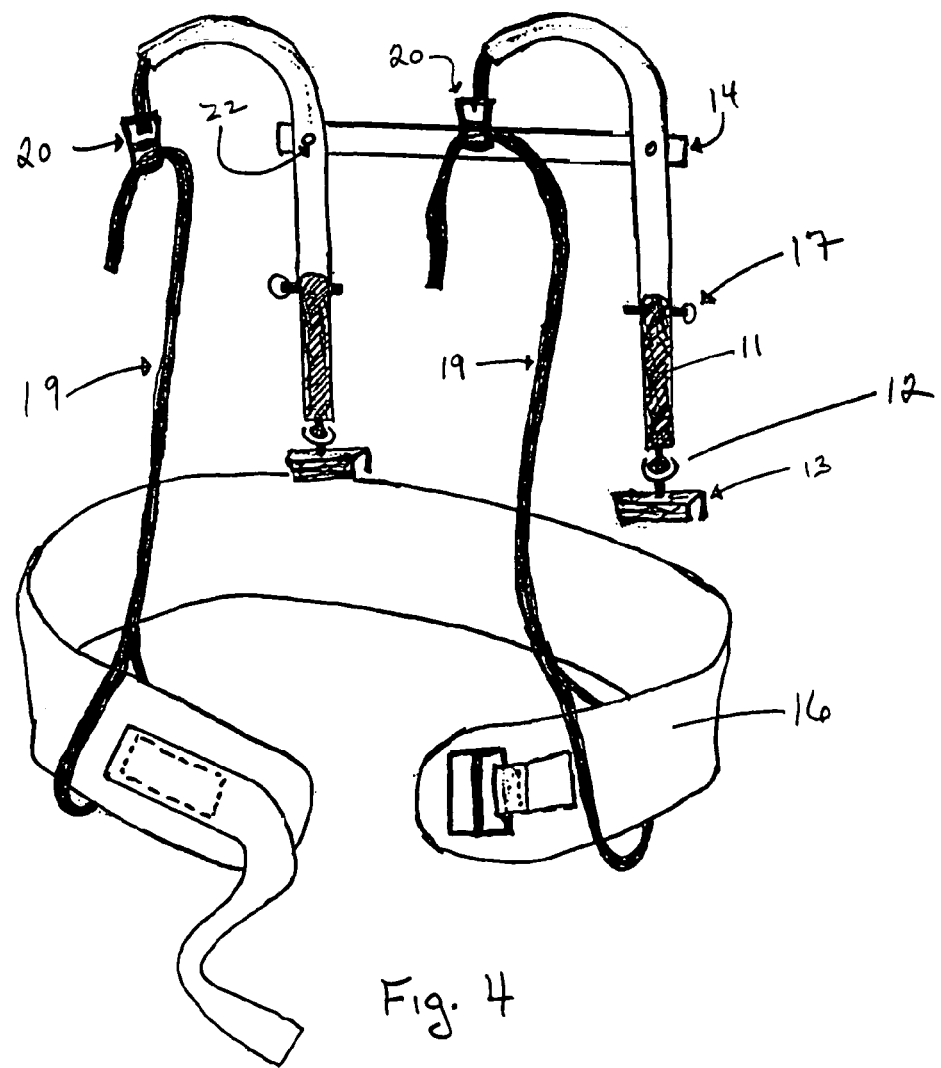
FIG. 4 is a perspective front view of the invention showing the garment support assembly, waist belt and front straps, per the preferred embodiment.

Further, a flexible strap 19, such as commonly available three-quarter inch wide nylon webbing, is attached, using standard fasteners such as sheet metal screws, to the upper and front ends of the shoulder support tube's respectively FIG. 4. Such straps continue downward and generally parallel with the front of the wearer's body attach to the fronts of the waist belt 16. These straps are fitted with common buckles 20 that allow the length of the straps to be adjusted.

In use FIG. 5, the waist belt 16 of the subject device is comfortably fastened around the waist of the wearer, above the wearer's hips, with the garment support assembly 21 attached to the waist belt. The upper portion of the cane shaped shoulder support tubes 10 are positioned over the respective shoulders of the wearer with the front straps 19 loosely attached between the waist belt 16 and the top/front end of the shoulder support tubes 10.

While the wearer is standing upright with arms at his/her sides, and with the assistance of a second person as may be needed, the shoulder support tube/support rod assembly is slideably lengthened along its vertical axis until the underside of the shoulder support tube is just at or above the top of the wearer's shoulder. The adjustment pin 17/locking collar 23 is used to set and maintain said position, such that the shoulder support tube/support rod assembly can not shorten/compressed below the point set by the adjustment pin/collar but, however, does remain free to extend/lengthen up to the full upward/extended range of travel determined by the length of the slot 19 in the side wall of the shoulder support tube 10 and the position of the post 20, installed in the support rod and disposed within said slot FIGS. 3 & 6. The front straps 19 are then tightened to further stabilize the garment support assembly 21.

The wearer may take note of the position of the adjustment pins/collars in/on the support rod 11 for reference the next time he/she dons the subject device, eliminating the need for adjustment or assistance in subsequent wearing of the subject device.

The protective garment is then donned, in a normal manner, over the subject device with the shoulder portions of the garment placed over the shoulder support tubes 10. In this manner, all or most all of the weight of the garment that would be born on the wearer's shoulders is born on the shoulder support tubes 10, being transferred down the articulating and adjustable garment support assembly 21 to the waist belt 16 and the waist/hip area of the wearer, without restricting the wearer's freedom and ease of back, torso, shoulder movement.

In this above described preferred embodiment of the subject device, the articulated unions 12/ball joints of the garment support assembly 21, plus the ability of the shoulder support tube/support rod units to independently lengthen, but not shorten below a selectable set point FIGS. 3 & 6 and the pivoted 22, parallel linkage of the two shoulder support tubes via the common horizontal back support bar 14 (all as described above) result in an ergonomic device that supports the weight of a protective garment, yet is free to move with the motion of the wearer and accommodate the wearer's full range of back, neck and shoulder movement. Further, the subject device is adjustable in its vertical length to fit persons of different heights without the need to change the position of the garment support assembly 21 relative to the waist belt 16. Still further, the subject device does not rely on the tightness of the belt around the wearer's waist to secure, position or stabilize the garment support assembly 21 of the said device.

This invention may also be executed with a single vertical garment support assembly, attached to the waist belt, generally located at the center of the wearer's back over the spine and continuing up toward the wearer's shoulders where it separates into two elements (such as in the shape of the letter Y) with the right element extending over the right shoulder and the left element extending over the left shoulder of the wearer.

In the above single vertical garment support assembly design, the vertical support assembly may have a pivot point located where the top right and left portions of the 'Y' join the central vertical portion of the Vertical Support. This, along with the vertical/linear movement of the Vertical Support previously described, allows the desired freedom of movement for the wearer, while transferring the weight of the garment to the waist/hips of the wearer.

Those skilled in the art will recognize numerous ways to modify the specifics of the above described embodiment to take an alternate form, from that set out in this description, without departing from the spirit and scope of the invention. Further, references to materials, construction methods, specific shapes and dimensions, utilities or applications are not intended to be limiting in any manner and deviation in such areas may occur and remain within the spirit and scope of the invention.

We claim:

1. A device to transfer the weight of a protective garment from the shoulder area of the wearer to the waist/hip area of the wearer when said garment is worn over said device, the device comprising;
    a. a waist belt around the waist area of the wearer;
    b. a garment support assembly comprised of at least one vertical support member of substantially ridged material having an upper section and a lower section that are slidably attached to one another, an articulating junction with an upper and a lower portion and a waist belt attachment portion, where;
        i. the slidable attachment of the upper and lower sections of the vertical support member includes a post protruding from the surface of one section of a vertical support member that travels in a slot located in the wall of the other section of the vertical support member when the upper and lower sections of the vertical support member are slidably moved relative to one another along their common vertical axis, and,
        ii. the slidable attachment of the upper and lower sections of the vertical support member includes at least one hole through the horizontal axis of only one section of a vertical support member where a removable pin may be inserted through this hole such that the presences of the removable pin limits only the slidable shortening of the vertical support member without limiting the full extension range of slidable travel of the upper and lower sections of the vertical support member, and further,
    c. the upper portion of the vertical support member extending over the shoulder of the wearer and the lower end of the vertical support member is joined to the upper portion of the articulating junction;
        iii. the lower portion of said articulating junction is joined to a waist belt attachment means; and
    d. the garment support assembly is attached to the waist belt.

2. The device of claim 1 where there are two or more vertical support members and at least two of the said support members are each connected to a common member, other than the waist belt.

3. The device of claim 1 where the slidable attachment of the upper and lower sections of the vertical support member includes 2 or more holes through the horizontal axis of only one section of a vertical support member where a removable pin may be inserted.

* * * * *